(12) United States Patent
Hu et al.

(10) Patent No.: US 10,976,322 B2
(45) Date of Patent: Apr. 13, 2021

(54) GALACTOSE ORAL COMPOSITION AND USE THEREOF

(71) Applicant: Avalon HepaPOC Limited, Hong Kong (CN)

(72) Inventors: Oliver Yoa-Pu Hu, Taipei (TW); Ping Yang, Taipei (TW); Cheng-Huei Hsiong, Taipei (TW)

(73) Assignee: AVALON HEPAPOC LIMITED, New Territories (HK)

(*) Notice: Subject to any disclaimer, the term of this patent is extended or adjusted under 35 U.S.C. 154(b) by 281 days.

(21) Appl. No.: 16/165,819

(22) Filed: Oct. 19, 2018

(65) Prior Publication Data
US 2020/0124609 A1    Apr. 23, 2020

(51) Int. Cl.
G01N 33/66    (2006.01)

(52) U.S. Cl.
CPC ......... *G01N 33/66* (2013.01); *G01N 2800/08* (2013.01)

(58) Field of Classification Search
CPC ................ G01N 33/66; G01N 2800/08
See application file for complete search history.

(56) References Cited

U.S. PATENT DOCUMENTS

| | | | |
|---|---|---|---|
| 6,544,954 B1 * | 4/2003 | Hu | A61K 9/0019 514/23 |
| 2006/0198886 A1 * | 9/2006 | Jenkins | A61K 9/2081 424/468 |
| 2015/0290228 A1 * | 10/2015 | Backstrom | A61K 9/20 424/133.1 |
| 2020/0069675 A1 | 3/2020 | Hu et al. | |

FOREIGN PATENT DOCUMENTS

WO    WO-2006060936 A1 * 6/2006 ............. G01N 33/66

OTHER PUBLICATIONS

Aitkenhead et al., "The pharmacokinetics of oral and intravenous nalbuphine in healthy volunteers", Br J Clin Pharmacol, 1988; pp. 264-268, vol. 25.

* cited by examiner

*Primary Examiner* — Jennifer Wecker
*Assistant Examiner* — Michael Paul Shimek
(74) *Attorney, Agent, or Firm* — Muncy, Geissler, Olds & Lowe, P.C.

(57) ABSTRACT

A galactose oral composition having galactose, an antioxidant and a buffer. The galactose oral composition contains 1%-80% by weight of galactose. The antioxidant is selected from Vitamin A, Vitamin C, Vitamin E, Ethylenediaminetetraacetic acid (EDTA), sodium bisulfite, flavonoids, polyphenols, Diethylenetriaminepentaacetic acid (DTPA), and NTA-Nitrilotriacetate acid (NTA). The buffer is selected from ascorbic acid buffer, citrate buffer, phosphate buffer, acetate buffer, carbonate buffer, and triethanolamine buffer. The galactose oral composition can be applied to detect individual galactose metabolic ability to assess liver function.

15 Claims, 8 Drawing Sheets

Certificate of Analysis for Finished Product (Copy prohibited without permission)     Page 1 of 1

| Code No. | PYCD37 | Product Name | G.S.P. Oral Solution 400mg/mL 100mL | Version No. | 00 |
|---|---|---|---|---|---|
| File No. | NE-37 | Mfg. Date | 06/01/15 | Batch Size | 910 V | Lot No. | CM-037A |
| Sample Quantity | | Testing | 33 V | | |
| | | Storage | N/A | | |

| Test Items | Specifications | Results |
|---|---|---|
| Appearance | A clear colorless solution filled in a 100mL bottle. | Conforms |
| Identification | The retention time of the major peak in the chromatogram of the *Assay solution* corresponds to that of the *Standard solution* as obtained in the Assay. | Conforms |
| pH | 3.5~5.5 | 4.3 |
| Volume variation | 100~105 mL | 102 mL |
| Sterility test | Bacteria............. ( — ) , Mold............. ( — ) | (-) |
| 5-Hydroxymethylfurfural and related substances | Not more than 0.80 | 0.02 |
| Assay | 90.0%~110.0% | 99.4% |

Figure 1

GALACTOSE ORAL COMPOSITION AND USE THEREOF

BACKGROUND OF THE INVENTION

Field of the Invention

The present invention relates to a galactose oral formula capable of being employed in detection of galactose blood concentration.

Brief Discussion of the Related Art

Galactose is an epimer of glucose and one of the main components of lactose. Galactose is mainly metabolized in the body by the liver and can be converted into glucose or, in turn, synthesized to glycogen stored in the liver. As liver disease has a significant effect on the metabolism of galactose, maximum galactose elimination capacity (GEC) and galactose single point (GSP) blood concentration can be used as indicators of clinical quantitative liver function.

GEC has been performed as a quantitative human liver function test for years. However, GEC tests require a number of blood samples to establish a standard curve, which has difficulties in clinical application. There are many studies using GSP to assess human liver function. Liver function includes hepatic blood flow status, hepatic enzyme status, or metabolic ability of galactose.

Tang H. S. and Hu O. Y. P. (Digestion 1992; 52: 222-231) have revealed that a variety of liver diseases such as chronic hepatitis, liver cirrhosis, and liver cancer can be accurately identified by the GSP method. Also, the GSP method can be used to assess residual liver function. The GSP method is recommended in the US Food and Drug Administration (FDA) benchmark, and has been proven to be an extremely simple and viable method to assess residual liver function, which has been verified by common liver diseases in our people. Furthermore, GSP has become one of the methods recommended for use in testing liver function in the Guidance for Industry published by the FDA.

In the past, a subject's blood galactose concentration was measured 60 minutes after rapid intravenous injection of 0.5 g/kg of galactose for three minutes when in fasting, to obtain a GSP value (in μg/ml). However, the intravenous injection is invasive, which brings psychological stress to the subject and causes tissue damage, pain, or potential complications. In particular, multiple attempts are often needed to make a successful injection in children of primary school and preschool who are unable to cooperate with and have thinner blood vessels.

Thus, how to design a non-invasive galactose formula which can be administered orally to the subjects and can be detected accurately by the GSP method has become an important topic to be solved by the present invention.

SUMMARY OF THE INVENTION

The purpose of the present invention is to provide a galactose oral composition comprising galactose, a buffer, and an antioxidant, wherein said galactose oral composition ranges the pH values from 2.0 to 10.0, and wherein said galactose comprises D-(+)-galactose, L-(−)-galactose, stable isotope galactose, galactose ring, or galactose derivatives.

To achieve the above purpose of the present invention, said antioxidant is selected from the group consisting of Vitamin A, Vitamin C, Vitamin E, sodium bisulfite, polyphenols, Ethylenediaminetetraacetic acid (EDTA), Diethylenetriaminepentaacetic acid (DTPA), flavonoids, and NTA-Nitrilotriacetate acid (NTA).

To achieve the above purpose of the present invention, said buffer is selected from a group including at least one of ascorbic acid buffer, citrate buffer, phosphate buffer, acetate buffer, carbonate buffer, and triethanolamine buffer.

To achieve the above purpose of the present invention, said galactose oral composition ranges the pH values from 3.0 to 6.0.

To achieve the above purpose of the present invention, said galactose oral composition is a food composition and/or a pharmaceutical composition.

To achieve the above purpose of the present invention, said galactose oral composition further includes at least one of emulsifier, colorant, flavoring agents, sweetener, preservatives, excipients, extenders, stabilizers, and dispersants.

To achieve the above purpose of the present invention, said sweetener is selected from a group including at least one of D-Sorbitol, D-Sorbitol Solution 70%, D-Xylitol, Glycyrrhizin, Trisodium Glycyrrhizinate, D-Mannitol, Saccharin, Saccharin Sodium, Sodium Cyclamate, Calcium Cyclamate, Aspartame, Steviol Glycoside, Licorice Extracts, Acesulfame Potassium, Ammoniated Glycyrrhizin, Monoammonium Glycyrrhizinate, Maltitol, Maltitol Syrup (Hydrogenated Glucose Syrup), Isomalt (Hydrogenated Palatinose), Lactitol, Monoglucuronyl Glycyrrhetic Acid, Thaumatin, Erythritol, Sucralose, and Neotame.

To achieve the above purpose of the present invention, said spice is selected from a group including at least one of cherry, lemon, lime, mandarin, orange, tangerine, mint, strawberry, banana, caramel, licorice, passion-fruit, peach, raspberry, tutti-frutti, grapefruit, vanilla, cream, chocolate, and grapes.

Another purpose of the present invention is to provide a kind of galactose oral composition mentioned above for the preparation of an agent for the detection of hepatic blood flow status, hepatic enzyme status, and metabolic ability of galactose.

To achieve the above purpose of the present invention, each oral dose of the galactose oral composition ranges from 0.01 g/kg to 5 g/kg.

Another purpose of the present invention is to provide a galactose composition, comprising galactose, a buffer, and an antioxidant; wherein said galactose composition ranges the pH values from 2.0 to 10.0; wherein said galactose composition keeps the original color under high temperature condition; wherein said galactose includes at least one of D-(+)-galactose, L-(−)-galactose, stable isotope galactose, galactose ring, and galactose derivatives.

To achieve the above purpose of the present invention, said high temperature is a temperature at 80° C. to 250° C.

To achieve the above purpose of the present invention, said galactose composition is a nutritional sweetener for diabetes.

To achieve the above purpose of the present invention, said galactose composition can be put into a food, nourishment, and formula milk.

Another purpose of the present invention is to provide a kind of galactose composition mentioned above for the preparation of an agent for the detection of hepatic blood flow status, hepatic enzyme status, and metabolic ability of galactose.

To achieve the above purpose of the present invention, each dose of the galactose composition ranges from 0.01 g/kg to 5 g/kg.

BRIEF DESCRIPTION OF THE DRAWINGS

FIG. 1 shows results of test report for the galactose oral solution products.

DETAILED DESCRIPTION OF THE PREFERRED EMBODIMENTS

Figure 2:
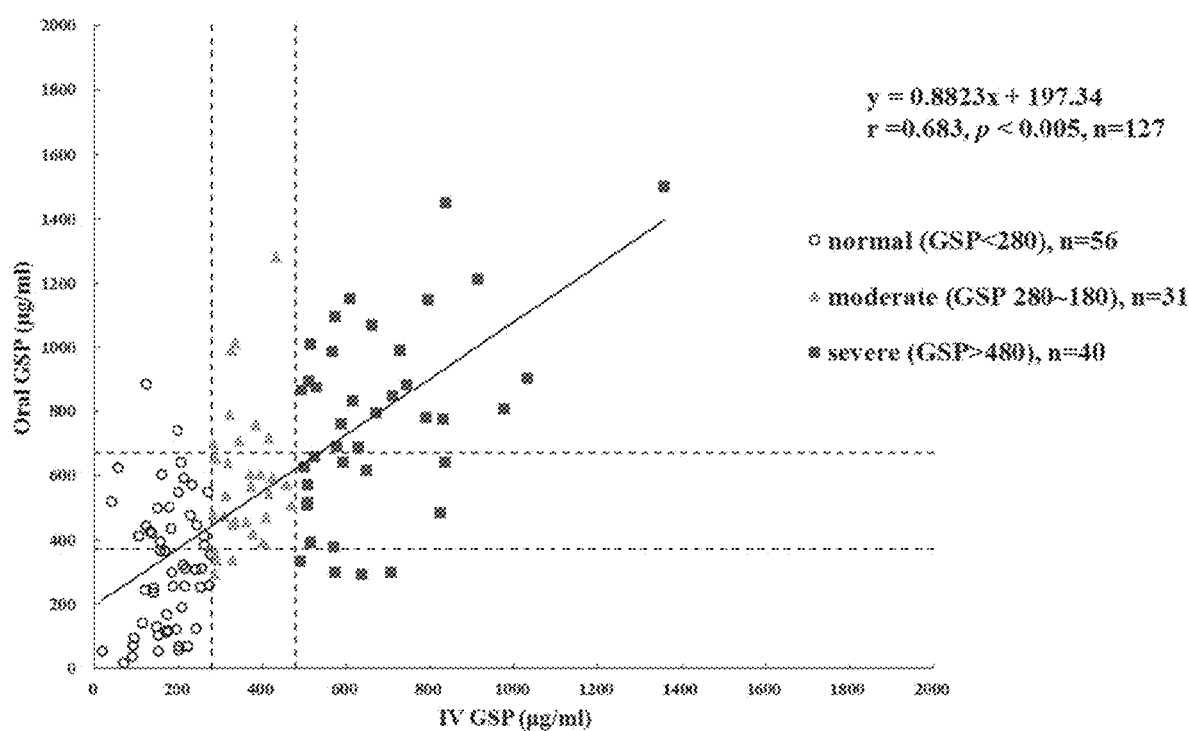
FIG. 2 shows a relative distribution view of the GSP results of galactose intravenous injection and the OGSP results of galactose oral administration.

The present invention is exemplarily illustrated but not limited by the following embodiments.

In the present invention, various kinds and concentrations of buffer, and antioxidants, are added for adjustment into a galactose oral solution in different pH values, and then the stability tests are carried out to provide a good galactose oral formula.

The present invention refers to a galactose of the present invention including at least one of D-(+)-galactose, L-(−)-galactose, and stable isotope galactose.

The present invention refers to an antioxidant of the present invention including at least one of Vitamin C and/or sodium bisulfite, Vitamin A, Vitamin E, Ethylenediaminetetraacetic acid (EDTA), Diethylenetriaminepentaacetic acid (DTPA), flavonoids, polyphenols, and NTA-Nitrilotriacetate acid (NTA).

The present invention refers to a buffer of the present invention including at least one of citrate buffer, phosphate buffer, acetate buffer, carbonate buffer, ascorbic acid buffer, and triethanolamine buffer.

Preparation of the Galactose Oral Solution:

50 liters of water at 45° C. are injected into a dispensing barrel and then 155 g sodium citrate is added and agitated until completely dissolved. After adjusting the pH value to 4.5±0.5, 500 g sodium bisulfite is added and agitated until completely dissolved, and 40 kg D-Galactose is added and agitated until completely dissolved, and then 36 g sodium citrate is added and agitated until completely dissolved. After adjusting the pH value to 4.5±0.5, the water at 45° C. is filled until the volume of the whole mixture reaches 100 liters, then stirred for 10 minutes and filtered with a 0.22 μm pore size filter. After mixing evenly, the mixture is poured into a number of glass bottles each with a capacity of 100 ml, then sampled and sealed immediately. Finally the bottles are put into a high-pressure steam pot at 121° C. (1.2 kg/cm$^2$). After sterilization for 15 minutes, the bottles are taken out and sampled. Table 1 is the results of long-term stability tests for the galactose oral solution. It is shown that the formula has good stability after 37-148 months of placement.

TABLE 1

Long-term stability of the galactose oral solution

| | Storage duration (month) | | | | | |
|---|---|---|---|---|---|---|
| | 37 | 60 | 65 | 88 | 126 | 148 |
| State | Qualified | Qualified | Qualified | Qualified | Qualified | Qualified |
| pH value | 3.8 | 3.8 | 3.5 | 3.6 | 3.8 | 3.9 |
| Turbidity | (—) | (—) | (—) | — | (—) | — |
| Ingredient (%) | 100 ± 5 | 98.1 | 103 ± 8 | 98.8 | 102 ± 1 | 99.3 |
| 5-hydroxymethyl-furfural | — | 0.07 | — | 0.08 | — | 0.06 |

(—) indicates no growth of bacteria and fungi
—indicates no detection

The content of the galactose is 1%-80%. The method is to configure the galactose at high temperature as 1%-80% solutions, and then dilute it to the better content of 4%-40% of the total weight. Do not add buffer or add buffer to the total weight of 0.001%-5%. Do not add antioxidant or add antioxidant to the total weight of 0.001%-5%. Appropriate oral solution formula can be prepared by selecting the buffer and antioxidant, and adding the content of the following ingredients: antioxidant of 0.001M-1M sodium bisulfite, and/or Vitamin C, Vitamin A, Vitamin E, flavonoids, Ethylenediaminetetraacetic acid (EDTA), polyphenols, Diethylenetriaminepentaacetic acid (DTPA), and/or NTA-Nitrilotriacetate acid (NTA); and/or buffer of one of seven solutions, namely 0.001M-1M citrate buffer, phosphate buffer, acetate buffer, carbonate buffer, ascorbic acid buffer, and triethanolamine buffer with adjustment of the pH values ranged 4.0-9.0. A stable oral solution formula can be obtained by adding 0.01% citrate buffer and 0.5% sodium bisulfite with the pH value of 4.5.

According to the oral solution prepared by the above formula, the concentration of galactose is 400 mg/ml and the volume thereof is 100 ml. The galactose oral solution product is then tested and the results are shown in FIG. 1. Based on the results in FIG. 1, the color, main ingredients, pH value, volume for the galactose oral solution of the present invention are in line with the standard value. According to the regulations of USP-XXII edition, for Dextrose oral liquid main decomposition products of 5-hydroxymethyl-furfural and other relevant regulations on the content of related substances, the absorbance value of the water as a blank control solution should not exceed 0.25 under the condition of Dextrose concentration 1/250 g/ml at 284 nm wavelength. The content of 5-hydroxymethyl-furfural in the galactose oral solution of the present invention after placing for a long time is only 0.02. Thus, according to the results in FIG. 1 and Table 1, the galactose oral solution of the present invention can be placed for a long time and maintain stability.

Embodiment 1

Effects of Antioxidant and Buffer on the Stability of the Galactose Oral Solution Preparing the galactose oral solution, the concentration of galactose is 4% and the volume is 100 ml. In the stability study, according to the results in Table 2, all the formulae of adding Vitamin C (0.5 M) as an antioxidant have changed the color of the oral solution after 168 hours under the condition of 80° C. However, when sodium bisulfite (0.1M, 0.5M) as the antioxidant and the pH value thereof is adjusted to 4.5, there is no change in color after placing the formula under the condition of 80° C. for 168 hours.

TABLE 2

|  | Formula | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Sol.pH | 7.35 | 7.35 | 4.5 | 4.5 | 7.35 | 7.35 | 4.5 | 4.5 | 7.35 | 4.5 |
| Bisulfite(M) | 0.5 |  | 0.5 |  | 0.1 |  | 0.1 |  |  |  |
| Vit.C(M) |  | 0.5 |  | 0.5 |  | 0.1 |  | 0.1 |  |  |
| Color after 168 hours | ** | ***** |  | **** | ** | *** |  | *** | * | * |

*: represents the color depth; the more "*" the deeper the color

Preparing the galactose oral solution, the concentration of galactose is 4% and the volume is 100 ml. In the stability study, five different buffers with each having 0.01M concentration and antioxidants are added respectively for formation, wherein the buffer is selected from the group including citrate buffer, phosphate buffer, acetate buffer, carbonate buffer and triethanolamine buffer, and the antioxidants are still sodium bisulfite and Vitamin C of 0.01M in concentration. According to the results in Table 3, all formulae of adding Vitamin C as the antioxidant have changed color after 168 hours, thus the stability is poor. However, all formulae of adding sodium bisulfite as the antioxidant, no matter in any buffer, there is no change in color under the condition of the pH value at 7.35 or 4.5. By observing the galactose of the formulae 1-30 under the condition of the pH value at 4.5, with citrate buffer and sodium bisulfite antioxidant, the stability is better in terms of the pH value and color change.

Preparing the galactose oral solution, the concentration of galactose is 4% and the volume is 100 ml. In the stability study, five different buffers with each having 1M concentration and antioxidants are added respectively for formation, wherein the buffer is selected from a group including citrate buffer, phosphate buffer, carbonate buffer and triethanolamine buffer, and the antioxidants are still sodium bisulfite or Vitamin C of 0.5M in concentration. According to the results in Table 4, all formulae of adding 0.5M Vitamin C as an antioxidant have changed color after 168 hours, so the stability is poor. And for the partial formulae in which 0.5M sodium bisulfite is added as an antioxidant, there are changes in color after 168 hours under the condition of 80° C. Besides, when storing in 1M carbonate buffer under the condition of the pH value at 7.35 and in 1M triethanolamine buffer under the condition of the pH value at 4.5 for a week, there are changes in color. Therefore, it is known that the stability of the formula will be reduced when

TABLE 3

|  | Formula | | | | | | | | | | | | | | | | | | | |
| --- | --- | --- | --- | --- | --- | --- | --- | --- | --- | --- | --- | --- | --- | --- | --- | --- | --- | --- | --- | --- |
|  | 11 | 12 | 13 | 14 | 15 | 16 | 17 | 18 | 19 | 20 | 21 | 22 | 23 | 24 | 25 | 26 | 27 | 28 | 29 | 30 |
| Citrate | ✓ | ✓ | ✓ | ✓ |  |  |  |  |  |  |  |  |  |  |  |  |  |  |  |  |
| Phosphate |  |  |  |  | ✓ | ✓ | ✓ | ✓ |  |  |  |  |  |  |  |  |  |  |  |  |
| Acetate |  |  |  |  |  |  |  |  | ✓ | ✓ | ✓ | ✓ |  |  |  |  |  |  |  |  |
| Carbonate |  |  |  |  |  |  |  |  |  |  |  |  | ✓ | ✓ | ✓ | ✓ |  |  |  |  |
| Triethanolamine |  |  |  |  |  |  |  |  |  |  |  |  |  |  |  |  | ✓ | ✓ | ✓ | ✓ |
| pH    4.5 |  |  | ✓ | ✓ |  |  | ✓ | ✓ |  |  | ✓ | ✓ |  |  | ✓ | ✓ |  |  | ✓ | ✓ |
|         7.35 | ✓ | ✓ |  |  | ✓ | ✓ |  |  | ✓ | ✓ |  |  | ✓ | ✓ |  |  | ✓ | ✓ |  |  |
| Bisulfite 0.1M | ✓ |  | ✓ |  | ✓ |  | ✓ |  | ✓ |  | ✓ |  | ✓ |  | ✓ |  | ✓ |  | ✓ |  |
| Vit.C 0.1M |  | ✓ |  | ✓ |  | ✓ |  | ✓ |  | ✓ |  | ✓ |  | ✓ |  | ✓ |  | ✓ |  | ✓ |
| Color after 168 hours |  | *** |  | **** |  | ** |  | ** |  | ** |  | ** |  | *** |  | *** |  | *** |  | *** |

*: represents the color depth; the more "*", the deeper the color;
+: represents amount of precipitation the concentration of the sodium bisulfite and the buffer increase together. When the remaining four buffers with high concentration, namely citrate buffer, phosphate buffer, carbonate buffer and triethanolamine buffer, are added into the antioxidant with high concentration of sodium bisulfite under the condition of the pH value at 4.5, they are more stable, but better in the environment of citrate buffer and acetate buffer. After placing the formulae 31-50 under the condition of 80° C. for a week, there is no precipitation.

solution and the antioxidant concentration of sodium bisulfite are adjusted, the results indicate that under acidic conditions and 1% antioxidant concentration of sodium bisulfite, both the pH value and absorbance value have the smallest changes before and after sterilization.

In 0.01M phosphate buffer, both the pH value of the oral solution and the antioxidant concentration of sodium bisulfite are adjusted. The results indicate that, under acidic conditions and 1% antioxidant concentration of sodium

TABLE 4

| | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|
| Citrate (M) | 1 | 1 | 1 | 1 | | | | | | | | | | | | | | | | |
| Phosphate (M) | | | | | 1 | 1 | 1 | 1 | | | | | | | | | | | | |
| Acetate (M) | | | | | | | | | 1 | 1 | 1 | 1 | | | | | | | | |
| Carbonate (M) | | | | | | | | | | | | | 1 | 1 | 1 | 1 | | | | |
| Triethanolamine (M) | | | | | | | | | | | | | | | | | 1 | 1 | 1 | 1 |
| pH | | | | | | | | | | | | | | | | | | | | |
| 4.5 | | | ✓ | ✓ | | | ✓ | ✓ | | | ✓ | ✓ | | | ✓ | ✓ | | | ✓ | ✓ |
| 7.35 | ✓ | ✓ | | | ✓ | ✓ | | | ✓ | ✓ | | | ✓ | ✓ | | | ✓ | ✓ | | |
| Bisulfite (M) | 0.5 | | 0.5 | | 0.5 | | 0.5 | | 0.5 | | 0.5 | | 0.5 | | 0.5 | | 0.5 | | 0.5 | |
| Vit.C (M) | | 0.5 | | 0.5 | | 0.5 | | 0.5 | | 0.5 | | 0.5 | | 0.5 | | 0.5 | | 0.5 | | 0.5 |
| Color after one week | * | ***** | | ***** | * | ***** | | ***** | | **** | | ***** | ** | ***** | | ***** | | **** | * | ***** |

*: represents the color depth; the more "*", the deeper the color

Embodiment 2

Effects of the pH Value on the Stability of the Galactose Oral Solution

The stability tests of the galactose oral solution are carried out with the pH values ranging from 5.02 to 8.52, wherein the galactose concentration is 4%, volume is 100 ml, and does not contain any buffers and antioxidants. Based on the regulations of USP-XXII edition, for Dextrose oral liquid main decomposition products of 5-hydroxymethyl-furfural and other relevant regulations on the content of related substances, the absorbance value of the water as a blank control solution should not exceed 0.25 under the condition of Dextrose concentration 1/250 g/ml at 284 nm wavelength. Accordingly, the corresponding absorbance value of the 4% concentration of the galactose oral solution prepared by the invention should not exceed 2.5. As a result, it is found that the variation of the formula is less before and after sterilization when the pH value is 4.5. Thus, it is known that under the low pH environment, stability is better.

Embodiment 3

Effects of Antioxidant Concentration on the Stability of the Galactose Oral Solution After observation on the stability of the galactose oral solution which is prepared with different antioxidant concentrations, it can be found that when the antioxidant concentration increases, both the pH value and the absorbance value have smallest changes before and after sterilization, and the stability in the situation where the antioxidant is added is better than that where the antioxidant is not added. In 0.01M citrate buffer, both the pH value of the oral bisulfite, both the pH value and absorbance value have the smallest changes before and after sterilization, and the stability is better. In 0.01M acetate buffer, both the pH value of the oral solution and the antioxidant concentration of sodium bisulfite are adjusted, the results indicate that under the condition of 1% antioxidant concentration of sodium bisulfite, both the pH value and the absorbance value have the smallest changes before and after sterilization, and the stability is better. In 0.01M triethanolamine buffer, both the pH value of the oral solution and the antioxidant concentration of sodium bisulfite are adjusted, the results indicate that under the condition of 1% antioxidant concentration of sodium bisulfite, both the pH value and the absorbance value have the smallest changes before and after sterilization, and the stability is better.

According to the smallest change in the pH value and the least change in the color of the solution, the optimal formula with citrate buffer can be selected as an ideal model system. Further study on raising the concentration of the galactose to 40%. In a pure water environment, the yellow color of the solution increases with the increase of the galactose concentration. In acidic citrate buffer, adding different concentrations of sodium bisulfite has little effect on the pH value before and after sterilization. However, when the concentration of sodium bisulfite is greater than 0.5%, the color of the oral solution is not changed, and the minimum changes of the absorbance value can also be obtained. In alkaline citrate buffer, no matter how much the concentration of sodium bisulfite is added, the color of the oral solution changes significantly after storing for a week at 80° C.

General sugars such as sucrose or galactose will discolor at elevated temperatures of about 80° C., and the galactose at high temperatures will discolor whether it is a solid or a solution. When the galactose oral solution formula of the present invention is placed at 80° C. for storage or 121° C. for high-temperature sterilization, there is no change in color. Accordingly, the galactose oral solution formula of the present invention can be used as a sweetness supplement in high temperature, such as in baking. Since the galactose has sweetness and calorie but does not affect blood sugar, it can also be a nutritional sweetener for diabetes or those who need to control the blood sugar.

The following further illustrates the feasibility study of applying the galactose oral composition formula to detect the concentration of the galactose in blood.

The conditions of the research object

Subject inclusion criteria:

1. Male or female in the ages between 20 and 85.
2. Those who agree to sign the subject consent and are willing to cooperate with all research procedures.

Subject exclusion criteria:

1. Patients who have had an allergic reaction to galactose and have galactosemia.
2. Those who have received the whole or subtotal gastrectomy, celiac disease and intestinal resection and have other medical history.
3. Diabetes.
4. Children or disabled.
5. Any other medical-related reasons certified by the principle investigator are ruled out in this test.

Research methods, procedures and related tests (1) Pre-screening

You must sign the subject consent prior to screening period and we will record your past medical history (including medication history) to assist the research physicians in qualifying you to participate in the study before using the studied medication and grouping your study.

(2) Starting the research

Each subject will undergo two additional liver function tests, i.e., GSP and OGSP, each of which will be studied over a period of time. The time interval between these two tests should be at least 12 hours. One needs to be fasting for 6 hours before the day of testing.

OGSP examination: Subjects drank 1.25 ml of galactose solution per kg of body weight (400 mg of galactose per ml), i.e. 0.5 g/kg of galactose per kg body weight. After drinking galactose oral solution for 3 to 5 minutes, at least 20 ml of water is given. After 60 minutes after finishing oral administration, blood is taken from the fingers to take 0.5 ml of whole blood for slowly dropping on the galactose test strip, then the examination is completed.

The galactose contains 1% to 80% of the total amount by weight, preferably, 4% to 40%, contains 0.001% to 5% with or without addition of buffer, and 0.001% to 5% with or without addition of the antioxidant. The antioxidant therein is selected from a group including at least one of Vitamin C and/or sodium bisulfite, Vitamin A, Vitamin E, polyphenols, Ethylenediaminetetraacetic acid (EDTA), Diethylenetriaminepentaacetic acid (DTPA), flavonoids, and/or NTA-Nitrilotriacetate acid (NTA). The buffer is selected from a group including at least one of citrate buffer, phosphate buffer, acetate buffer, carbonate buffer, ascorbic acid buffer, and triethanolamine buffer.

GSP: Subjects are injected with 1.25 ml of galactose injection per kg of body weight (400 mg of galactose per ml), i.e. 0.5 g/kg of galactose per kg body weight. The galactose injection is completed within 3 to 5 minutes. After 60 minutes after finishing injection, blood is taken from the fingers to take 0.5 ml of whole blood for slowly dropping on the galactose test strip, then the examination is completed.

Embodiment 4

Figure 3:
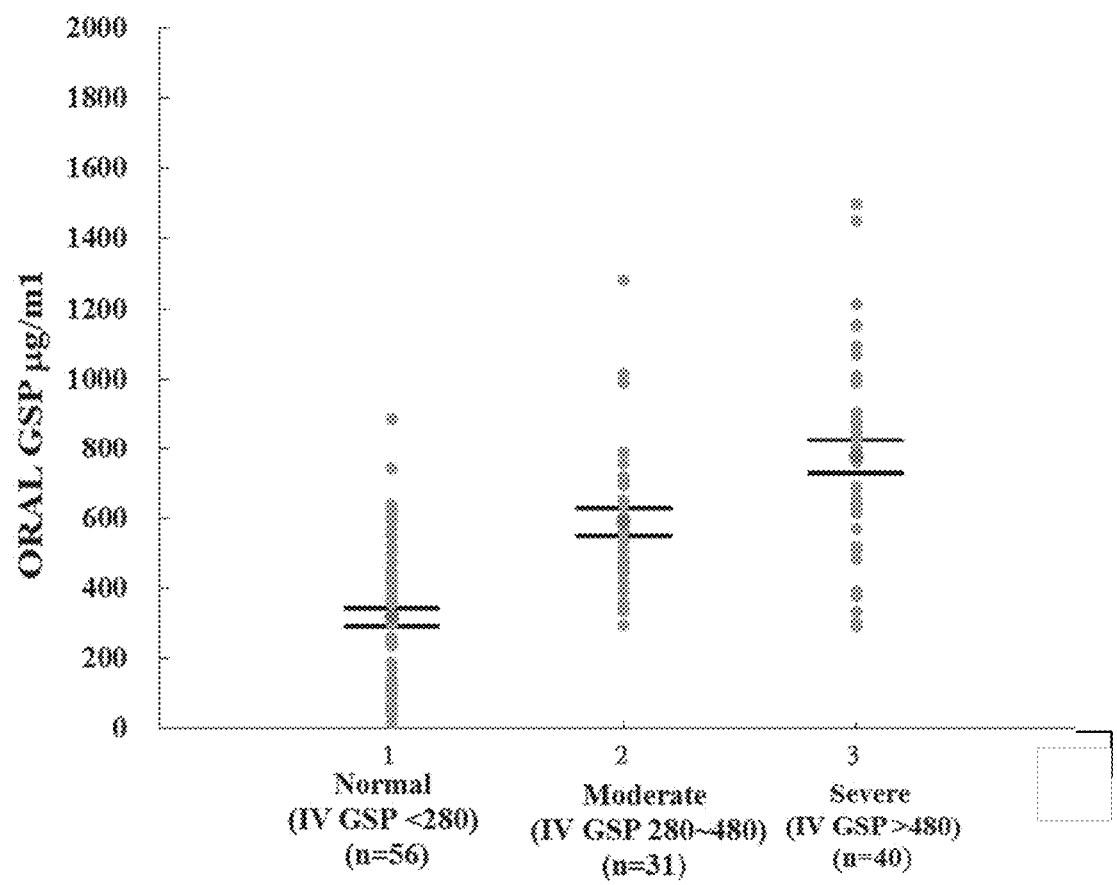
FIG. 3 shows a distribution view of the OGSP results of the galactose oral administration for subjects with normal, moderately-impaired and severely-impaired liver functions.
Figure 5:
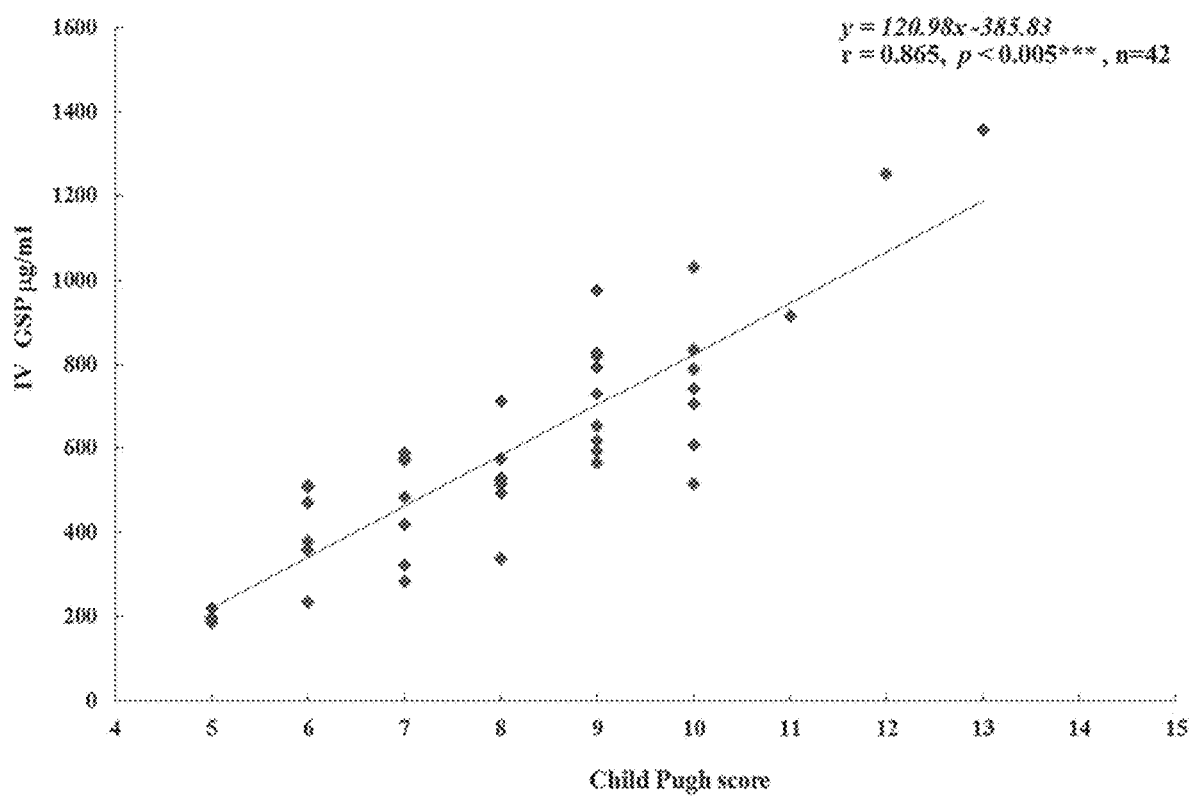
FIG. 5 shows a correlation between the GSP results of the galactose intravenous injection and cirrhosis.

The OGSP Results of the Galactose Oral Administration and the GSP Results of the Galactose Intravenous Injection FIGS. 2 and 3 are relative distribution views of the GSP results of the galactose intravenous injection and the OGSP results of the galactose oral administration for 127 subjects (56 in normal liver function and 71 in impaired liver function). According to Digestion 1992; 52: 222-231 recommendations, subjects were divided into 3 groups with GSP values (GSP) of intravenously administered galactose, wherein GSP<280 µg/ml is defined to indicate that the subject is in normal liver function, 280<GSP<480 µg/ml is defined to indicate that the subject is in moderately-impaired liver function, and GSP>480 µg/ml is defined to indicate that the subject is in severely-impaired liver function. According to results in FIGS. 2 and 3, the OGSP value for the oral galactose is higher than that for intravenous galactose and the OGSP value for oral galactose increases with severity of impaired liver function, and the OGSP and the GSP were positively correlated. Subjects in group of normal liver function have a galactose oral administration OGSP of 318±27 µg/ml (mean±standard error SE), with a minimum of 18 µg/ml and a maximum of 887 µg/ml. Subjects with mild or moderate liver function impairment have a galactose oral administration OGSP of 590±40 µg/ml (mean±standard error SE), with a minimum of 294 µg/ml and a maximum of 1282 µg/ml. Subjects with severe liver function impairment have a galactose oral administration OGSP of 777±48 µg/ml (mean±standard error SE), with a minimum of 293 µg/ml and a maximum of 1499 µg/ml. FIG. 5 shows the OGSP results of the galactose oral administration and the GSP results of the galactose intravenous injection for three groups of subjects. As shown from the results, the OGSP value of the galactose oral administration increases with the severity of impaired liver function. In particular, the OGSP value for the oral galactose is higher than that for the intravenous galactose. According to results in FIGS. 2, 3 and Table 5, it can be determined that the main range (mean±2 times standard error SE) of the OGSP galactose oral administration for the subjects in the group of normal liver function is about between 264 to 372 µg/ml, the main range (mean±2 times standard error SE) of the OGSP galactose oral administration for the subjects in the group of mildly or moderately impaired liver function is about between 510 to 670 µg/ml, and the main range (mean±2 times standard error SE) of the OGSP galactose oral administration for the subjects in the group of severely impaired liver function is about between 681 to 873 µg/ml. Even if the subject's results differ from person to person, the OGSP galactose oral administration for the subjects in the group of normal liver function does not exceed 670 µg/ml and the OGSP for subjects with impaired liver function may be larger than 370 µg/ml. Thus the subjects who have the OGSP greater than 370 µg/ml should acquire further liver function detection.

TABLE 5

The GSP results of the galactose intravenous injection and OGSP results of the galactose oral administration (mean ± standard error SE)

|  | Normal liver function (N = 56) | Mildly or moderately impaired liver function (N = 31) | Severely impaired liver function (N = 40) |
| --- | --- | --- | --- |
| IV GSP(μg/ml) [Digest 1992; 52: 222-231] | 247 ± 16.5*** | 423 ± 26.0*** | 630 ± 41.0*** |
| IV GSP (μg/ml) | 174 ± 8*** | 359 ± 10*** | 667 ± 29*** |
| OGSP(μg/ml) | 318 ± 27*** | 590 ± 40*** | 777 ± 48*** |

***$P < 0.005$ (ANOVA & LSD analysis)

Embodiment 5

Figure 6:
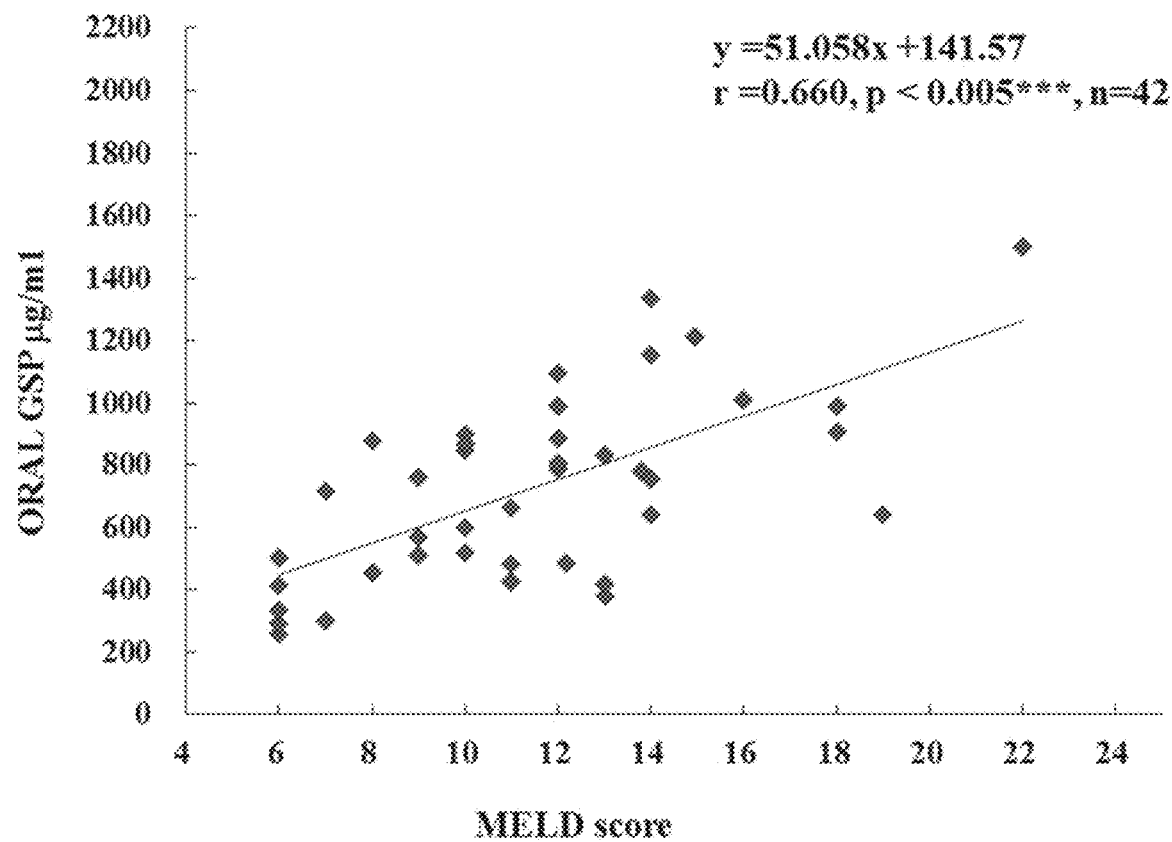
FIG. 6 shows a correlation between the OGSP results of the galactose oral administration and the score system for end-stage liver disease.

Correlation Between Blood Biochemical Values and the OGSP Results of the Galactose Oral Administration, the GSP Results of the Galactose Intravenous Injection 127 subjects (except diabetics) were divided into 3 groups with GSP values (GSP) of intravenously administered galactose, wherein GSP<280 μg/ml is defined to indicate that the subject is in normal liver function, 280<GSP<480 μg/ml is defined to indicate that the subject is in moderately-impaired liver function, and GSP>480 μg/ml is defined to indicate that the subject is in severely-impaired liver function. FIG. 6 shows the correlation between blood biochemical values and the OGSP results of the galactose oral administration, the GSP results of the galactose intravenous injection for three groups of subjects. The results show that GSP values of the intravenous galactose and OGSP values of the oral galactose are significantly correlated with a number of blood biochemical indexes, wherein AST (aspartate aminotransferase), ALT (alanine aminotransferase) are indicators of liver impairment, and the correlation between OGSP values of the oral galactose and AST, ALT is greater than that between GSP values of the intravenous galactose and AST, ALT.

TABLE 6

Correlation between blood biochemical values and GSP values of the intravenous galactose or the oral galactose for subjects (except diabetes)

|  | GSP (n = 127) | OGSP ( n = 127) |
| --- | --- | --- |
| AST | r = 0.431*** | r = 0.448*** |
| ALT | r = 0.153* | r = 0.212* |
| Total Bilirubin | r = 0.153*** | r = 0.178 |
| PT | r = 0.342*** | r = 0.129 |
| γ-GT | r = 0.091 | r = 0.290* |
| Albumin | r = −0.268* | r = −0.141 |
| ALP | r = 0.055 | r = 0.097 |
| Glucose | r = 0.193* | r = 0.142 |
| Uric acid | r = 0.052 | r = −0.012 |
| Cr | r = 0.112 | r = 0.070 |
| BUN | r = 0.080 | r = −0.130 |

*$P < 0.05$,
**$P < 0.01$,
***$P < 0.005$.

Embodiment 6

Figure 4:
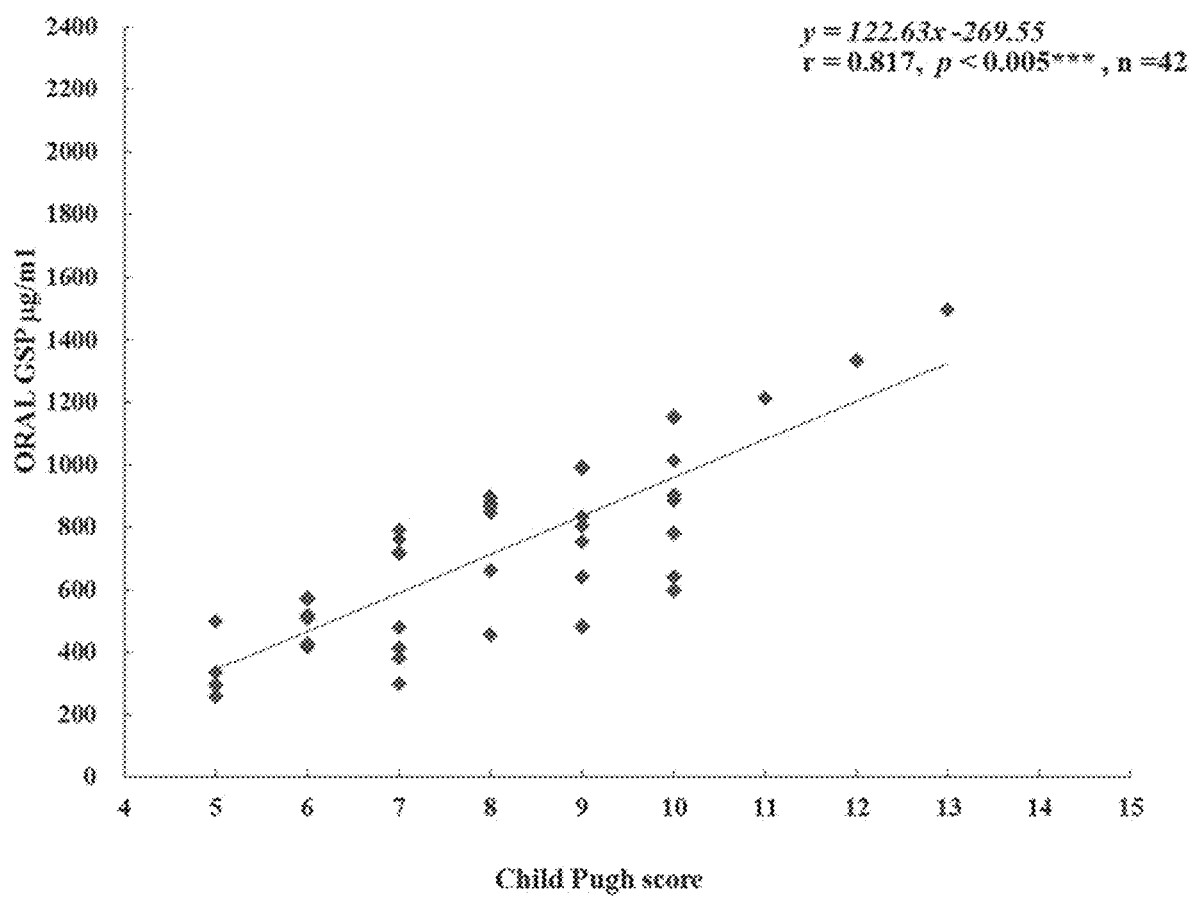
FIG. 4 shows a correlation between the OGSP results of the galactose oral administration and cirrhosis.

Correlation Between OGSP Values of the Oral Galactose, GSP Values of the Intravenous Galactose and Severe Live Disease GSP analysis is conducted on 42 patients with cirrhosis by galactose oral administration. FIG. 3 shows correlation between OGSP results of the oral galactose and cirrhosis. Typically, Child Pugh index (Child Pugh score) is clinically used to estimate the severity of cirrhosis. FIG. 4 shows that OGSP value of the oral galactose is positively correlated with Child Pugh index (r=0.817, p<0.005). Compared with GSP results of conventionally-intravenous galactose (FIG. 5), the OGSP value of the oral galactose is higher. However, both OGSP value of the oral galactose and GSP value of the intravenous galactose are positively correlated with cirrhosis. Accordingly, both OGSP value of the oral galactose and GSP value of the intravenous galactose have the same ability of estimating cirrhosis.

Figure 7:
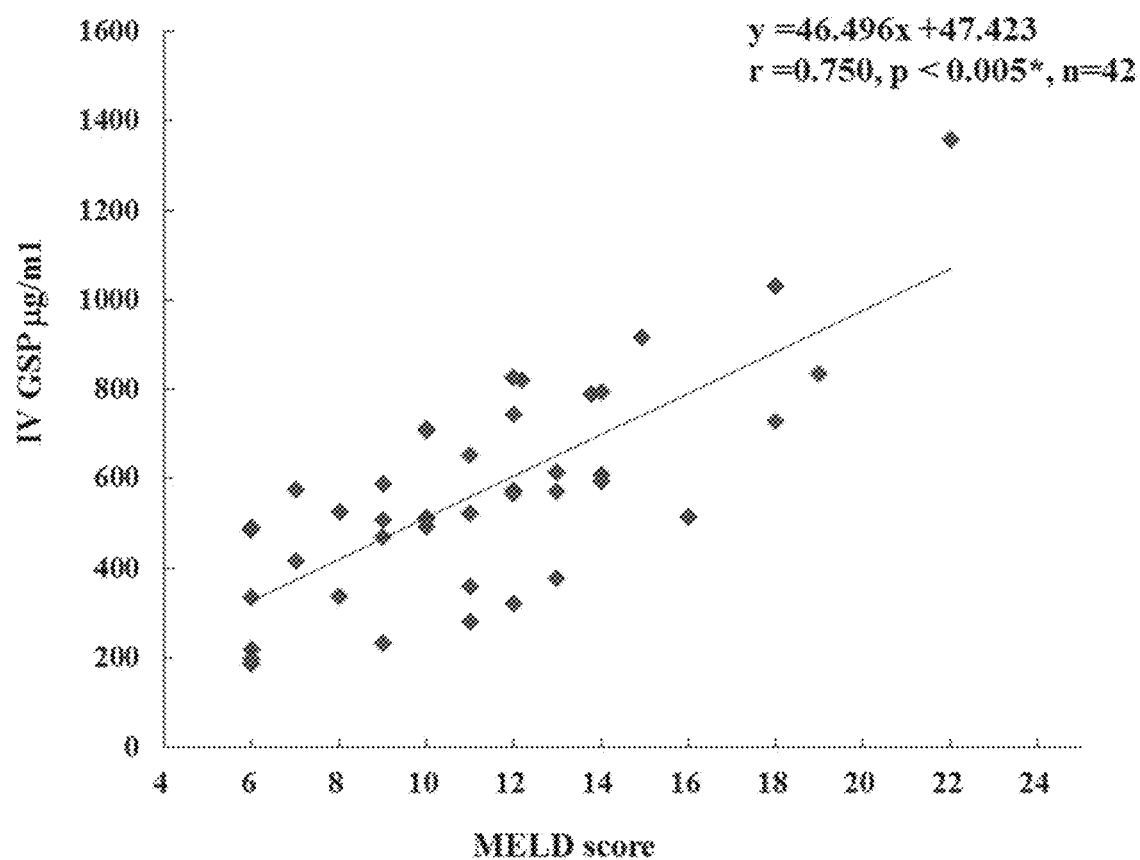
FIG. 7 shows a correlation between the GSP results of the galactose intravenous injection and the score system for end-stage liver disease.

MELD (Model for End-Stage Liver Disease) can predict the short-term and medium-term mortality of end-stage liver disease effectively, and its evaluation index is obtained simply, objective and easy to calculate. It is widely used in the diagnosis and treatment of liver diseases. OGSP analysis is conducted on 42 patients with cirrhosis by the galactose oral administration. FIG. 5 shows correlation between OGSP results of the oral galactose and MELD. FIG. 6 shows that OGSP value of the oral galactose is positively correlated with MELD (r=0.660, p<0.005). Compared with GSP results of the conventionally-intravenous galactose (FIG. 7), OGSP value of the oral galactose is higher. However, both OGSP value of oral galactose and GSP value of the intravenous galactose are positively correlated with MELD. Accordingly, both OGSP value of the oral galactose and GSP value of the intravenous galactose have the same ability of estimating MELD.

Embodiment 7

OGSP Changes of the Oral Galactose for Mouse with NASH (Non-Alcoholic Steatohepatitis)

Figure 8:
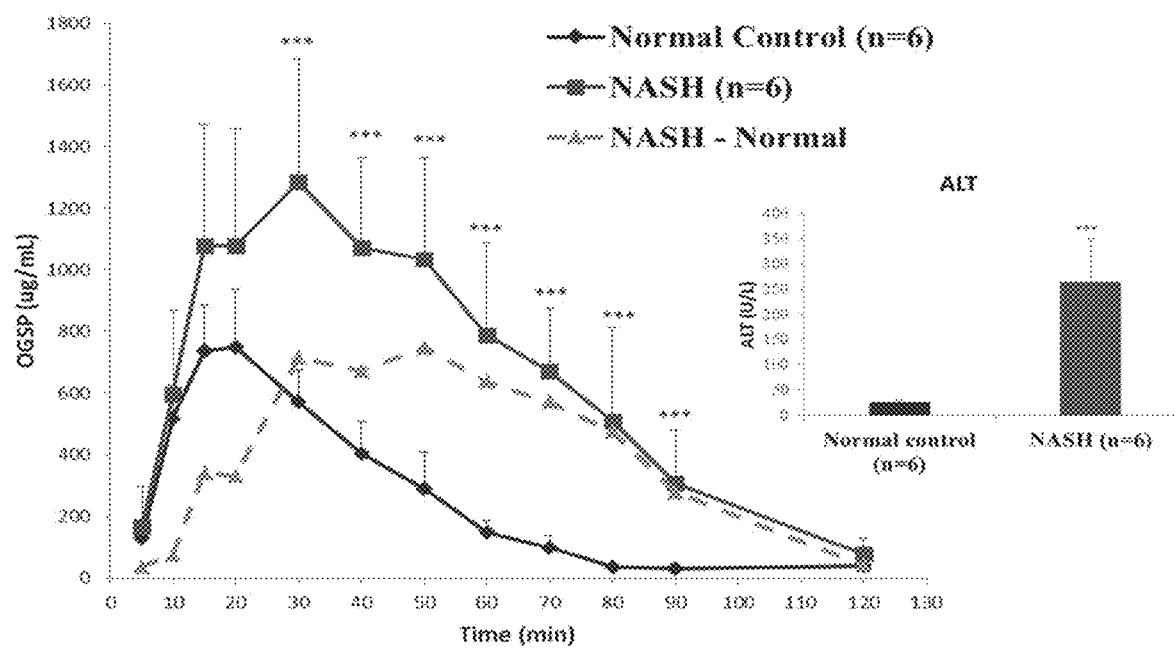
FIG. 8 shows the OGSP changes at various time points after oral administration of galactose to non-alcoholic steatohepatitis (NASH) animals.

FIG. 8 shows the OGSP results (OGSP) at each time point after the galactose oral administration. The mouse is led to non-alcoholic hepatitis (NASH) by being fed with high-fat diets. All animals with NASH have OGSP value that is higher than the value of normal individuals within 10 to 90 minutes after oral administration, wherein OGSP value changes a lot within 30 to 90 minutes after the oral administration. The results show that GSP value of the oral galactose has the ability of estimating NASH and is tested optimally from 30 to 80 minutes after the oral administration of the galactose.

The above-mentioned detailed description aims to specifically illustrate the practicable embodiments of the present invention, but the embodiments are not for limiting the patent scope of the present invention and all equivalent embodiments or modifications made without departing from the spirit of the present invention shall be contained within the patent scope of the present invention.

The present invention has the following advantages over the prior art:

(1) The galactose oral composition of the present invention is a non-invasive galactose formula, and can be administered to the subject orally for the GSP method;

(2) The galactose oral composition formula keeps good quality after long-time storage and high-temperature sterilization, and has good stability and performance; and (3) The galactose oral composition of the present invention has the ability of detecting galactose metabolism which is no less than that of the intravenous galactose.

What is claimed is:

1. A galactose oral composition, comprising:
   galactose;
   a buffer; and
   an antioxidant in an amount of from about 0.001 to about 99 percent by volume;
   wherein said galactose oral composition has a pH values ranging from 3.0 to 6.0; and
   wherein said galactose includes at least one of D-(+)-galactose, L-(−)-galactose, stable isotope galactose, galactose ring, or galactose derivatives.

2. The galactose oral composition according to claim 1, wherein said antioxidant is selected from the group consisting of Vitamin A, Vitamin C, Vitamin E, sodium bisulfite, polyphenols, Ethylenediaminetetraacetic acid (EDTA), flavonoids, Diethylenetriaminepentaacetic acid (DTPA), and NTA-Nitrilotriacetate acid (NTA).

3. The galactose oral composition according to claim 1, wherein said buffer is selected from the group consisting of ascorbic acid buffer, citrate buffer, phosphate buffer, acetate buffer, carbonate buffer, and triethanolamine buffer.

4. The galactose oral composition according to claim 1, wherein said galactose oral composition is a food composition and/or a pharmaceutical composition.

5. The galactose oral composition according to claim 1, wherein said galactose oral composition further includes at least one of emulsifier, colorant, spice, flavoring agents, sweetener, preservatives, excipients, extenders, stabilizers, dispersants, acceptable food additives or acceptable pharmaceutical excipients.

6. The galactose oral composition according to claim 1, wherein said galactose oral composition further include a sweetener, wherein said sweetener is selected from the group consisting D-Sorbitol, D-Sorbitol Solution 70%, D-Xylitol, Glycyrrhizin, Trisodium Glycyrrhizinate, D-Mannitol, Saccharin, Saccharin Sodium, Sodium Cyclamate, Calcium Cyclamate, Aspartame, Steviol Glycoside, Licorice Extracts, Acesulfame Potassium, Ammoniated Glycyrrhizin, Monoammonium Glycyrrhizinate, Maltitol, Maltitol Syrup (Hydrogenated Glucose Syrup), Isomalt (Hydrogenated Palatinose), Lactitol, Monoglucuronyl Glycyrrhetic Acid, Thaumatin, Erythritol, Sucralose, and Neotame.

7. The galactose oral composition according to claim 1, wherein said galactose oral composition further include a spice, wherein said spice is selected from the group consisting of cherry, lemon, lime, mandarin, orange, tangerine, mint, strawberry, banana, caramel, licorice, passion-fruit, peach, raspberry, tutti-frutti, grapefruit, vanilla, cream, chocolate, and grape.

8. A method of assessing hepatic blood flow status, hepatic enzyme status, and metabolic ability of galactose in a subject, comprises:
   a) administering orally to said subject a galactose oral composition comprising a galactose;
   b) collecting a biological specimen from said subject; and
   c) measuring an amount of galactose in said biological specimen to assess hepatic blood flow status, hepatic enzyme status, and metabolic ability of galactose in said subject.

9. The method according to claim 8, wherein each oral dose of the galactose oral composition ranges from 0.01 g/kg to 5 g/kg.

10. A galactose oral composition, comprising:
    galactose;
    a buffer; and
    an antioxidant in an amount of from about 0.001 to about 99 percent by volume;
    wherein said galactose composition has a pH value ranging from 3.0 to 6.0;
    wherein said galactose composition keeps the original color under high temperature condition; and
    wherein said galactose includes at least one of D-(+)-galactose, L-(−)-galactose, stable isotope galactose, galactose ring, or galactose derivatives.

11. The galactose oral composition according to claim 10, wherein said high temperature is 80° C. to 250° C.

12. The galactose oral composition according to claim 10, wherein said galactose composition is a nutritional sweetener.

13. The galactose oral composition according to claim 10, wherein said galactose composition can be put into a food, nourishment, and formula milk.

14. A method of assessing hepatic blood flow status, hepatic enzyme status, and metabolic ability of galactose in a subject, comprises:
    a) administering orally to said subject the galactose oral composition of claim 10;
    b) collecting a biological specimen from said subject; and
    c) measuring an amount of galactose in said biological specimen to assess hepatic blood flow status, hepatic enzyme status, and metabolic ability of galactose in said subject.

15. The method according to claim 14, wherein each dose of the galactose oral composition ranges from 0.01 g/kg to 5 g/kg.

* * * * *